United States Patent
Murray et al.

(10) Patent No.: US 7,126,142 B2
(45) Date of Patent: Oct. 24, 2006

(54) SOURCE LOADING APPARATUS FOR IMAGING SYSTEMS

(75) Inventors: Thomas R. Murray, Delafield, WI (US); Hani Ikram Noshi, Waukesha, WI (US); Timithoy F. Hamers, Wind Lake, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 314 days.

(21) Appl. No.: 10/285,014

(22) Filed: Oct. 31, 2002

(65) Prior Publication Data

US 2004/0086084 A1    May 6, 2004

(51) Int. Cl.
*G21F 5/02* (2006.01)
(52) U.S. Cl. ............... 250/497.1; 250/496.1; 250/493.1
(58) Field of Classification Search ............. 250/496.1, 250/497.1, 498.1, 505.1, 506.1, 507
See application file for complete search history.

(56) References Cited

U.S. PATENT DOCUMENTS

| 4,235,454 A | 11/1980 | Gray et al. |
| 4,501,011 A | 2/1985 | Hauck et al. |
| 4,791,934 A | 12/1988 | Brunnett |
| 5,036,899 A * | 8/1991 | Mullet ..................... 160/189 |
| 5,594,638 A | 1/1997 | Iliff |
| 5,711,297 A | 1/1998 | Iliff |
| 5,724,968 A | 3/1998 | Iliff |
| 5,821,541 A | 10/1998 | Tümer |
| 5,834,780 A | 11/1998 | Morgan et al. |
| 5,868,669 A | 2/1999 | Iliff |
| 5,910,107 A | 6/1999 | Iliff |
| 6,022,315 A | 2/2000 | Iliff |
| 6,113,540 A | 9/2000 | Iliff |
| 6,160,263 A | 12/2000 | Smith et al. |
| 6,201,247 B1 | 3/2001 | Lutheran et al. |
| 6,206,829 B1 | 3/2001 | Iliff |
| 6,434,216 B1 | 8/2002 | Maki et al. |

* cited by examiner

*Primary Examiner*—David A. Vanore
(74) *Attorney, Agent, or Firm*—Hunton & Williams LLP

(57) ABSTRACT

A transmission source loading apparatus for an imaging system utilizing a transmission source is disclosed. The source loading apparatus comprises a storage container for storing the transmission source, and a translation device. The translation device is adapted for advancing the transmission source from the storage container into a holder device for use of the imaging system. A gantry for an imaging system utilizing a transmission source is also disclosed. The gantry includes a gantry housing, a detector ring, a holder device for rotating the transmission source in a rotation path associated with the detector ring, and a transmission source loading apparatus.

24 Claims, 11 Drawing Sheets

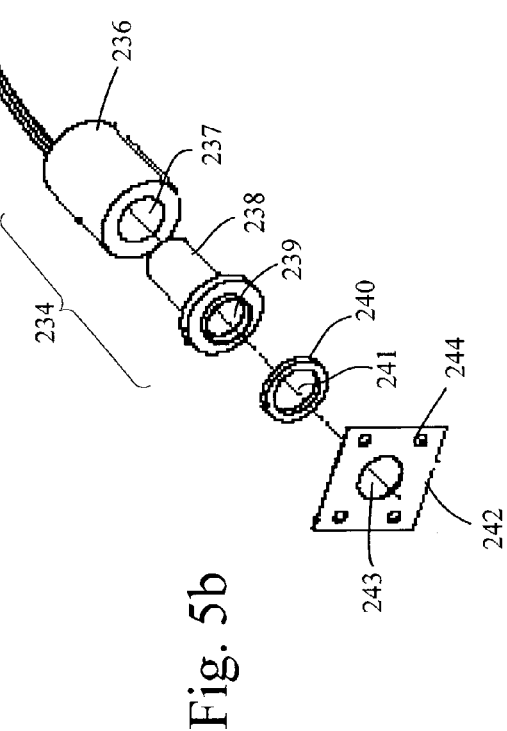
Fig. 5a
Fig. 5b

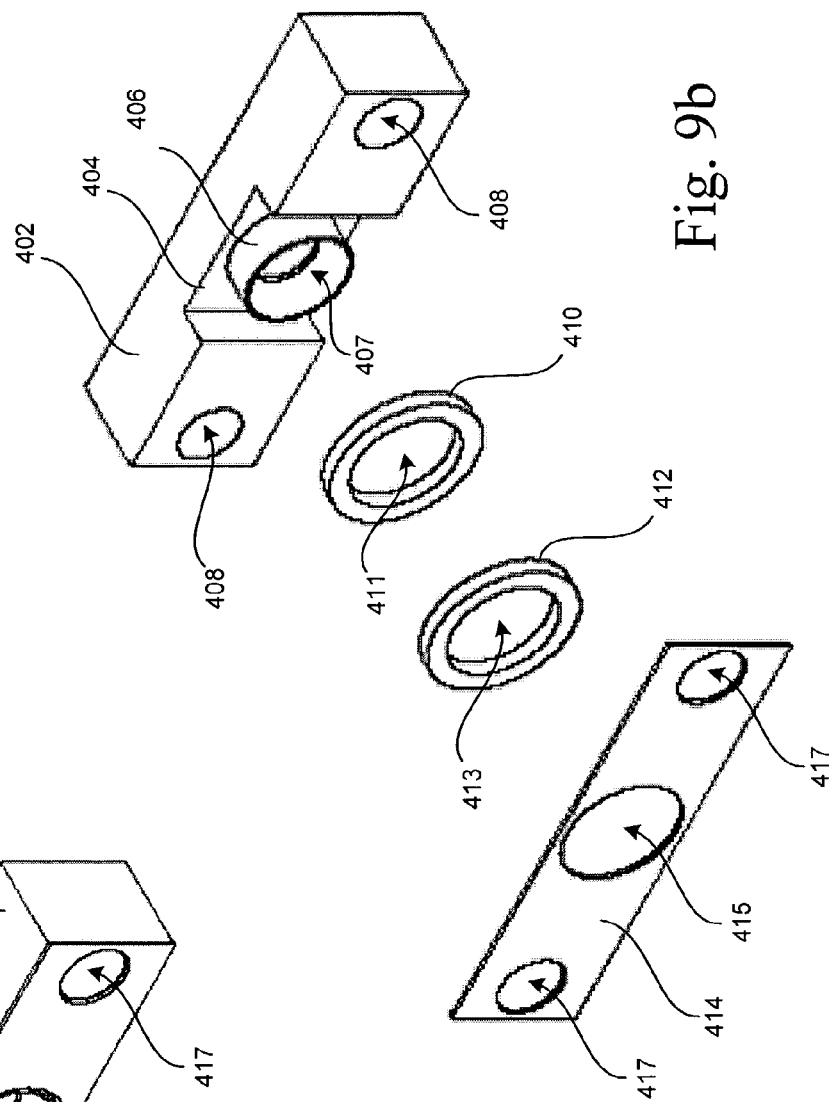
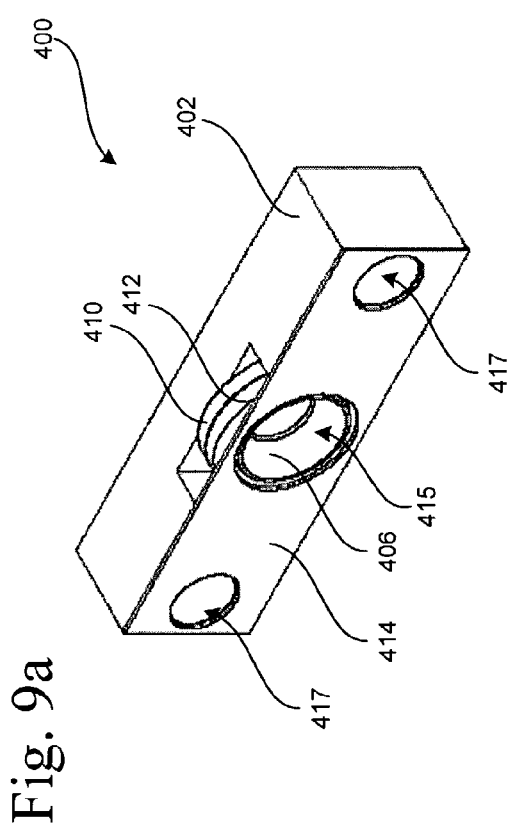
Fig. 9a
Fig. 9b

SOURCE LOADING APPARATUS FOR IMAGING SYSTEMS

BACKGROUND OF THE INVENTION

The invention relates generally to systems and methods for loading transmission sources used in imaging systems.

Imaging systems play an important role in the practice of medicine and the administration of health care to patients. Imaging systems allow physicians to diagnose otherwise undetectable problems throughout the body. For example, Positron Emission Tomography ("PET") imaging systems allow a physician to examine the heart, brain, and other organs, by producing images that show the chemical functioning of an organ or tissue. Most PET imagers operate by placing a patient on a cradle and moving the cradle into the gantry's patient bore, where the scanning takes place. The patient bore is lined by a series of detector rings that gather imaging data when the imager is scanning. The detector rings utilize crystals to measure coincidence events when radiation is released into the scanning area. The necessary radiation is released when a transmission source, or radioactive source, is rotated by a transmission ring around the inside perimeter of the detector rings. The data gathered by the crystals is used to produce the medical image of the patient's body.

The transmission source is often constructed of radioactive material, which can be harmful to humans after prolonged exposure. Accordingly, the transmission source for an imaging system must be kept within a shielded container until the imaging system is ready for use. Transferring the transmission source from the shielded container to a location where it can be rotated around the detector rings has presented several problems.

For example, some conventional PET imaging systems utilize a robotic arm to transfer the transmission source from the shielded storage container to the transmission ring. One disadvantage of the robotic arm is that it requires several mechanical movements including both rotation and translation. More specifically, the robotic arm must extend into the storage container to take hold of the transmission source, and pull out of the storage container without dropping the transmission source or letting it come into contact with any other structures. Outside the storage container, the robotic arm must once again move into position with the transmission ring. Each of these difficult movements is controlled by complex logic sequences governing the movements of the armature and transmission source. In addition, the reliability of this robotic armature is highly dependant on several geometric and dimensional tolerances based on the length of the robotic armature, and the cantilevered mount attached to the translation gearbox. The accuracy and reliability of the robotic armature is extremely important given that the transmission source must be precisely positioned within the transmission ring while in use, and in the storage container when not in use.

An additional disadvantage is that these robotic arms utilize a mechanical claw-like means, which must hold and at appropriate times release the transmission source. This design occasionally results in the transmission source being dropped during transfer.

For at least these reasons, there is a need for the continuous support of transmission sources at all times during loading and unloading. There is also the need for simplifying the rotational and translational paths the transmission source must take when moving from storage to loading positions. There is also a need for simplifying and improving the mechanical means used to grip and hold the transmission source during loading and unloading. Overcoming these disadvantages will lower the risk of the transmission source being dropped, which in turn will reduce imaging system downtime.

The invention provides apparatuses, systems and methods for source loading in imaging systems, that overcome the disadvantages of known systems and methods while offering features not present in known systems and methods.

BRIEF SUMMARY OF THE INVENTION

In accordance with one embodiment of the invention, a transmission source loading apparatus for an imaging system utilizing a transmission source is disclosed. The source loading apparatus comprises a storage container for storing the transmission source, and a translation device. The translation device is adapted for advancing the transmission source from the storage container into a holder device for use of the imaging system.

In another embodiment of the invention, a gantry for an imaging system utilizing a transmission source is disclosed. The gantry includes a gantry housing, a detector ring, a transmission ring and holder device for rotating the transmission source in a rotation path associated with the detector ring, and a transmission source loading apparatus. The source loading apparatus includes a storage container for storing the transmission source, and a translation device. The translation device is adapted for advancing the transmission source from the storage container into a holder device for use of the imaging system.

In yet another embodiment of the invention, a transmission source loading apparatus for an imaging system utilizing a transmission source is disclosed. The apparatus is comprised of a means for storing the transmission source and a means for advancing the transmission source from the storage means into a means for rotating the transmission source for use of the imaging system.

BRIEF DESCRIPTION OF THE DRAWINGS

The present invention can be more fully understood by reading the following detailed description of the presently preferred embodiments together with the accompanying drawings, in which like reference indicators are used to designate like elements, and in which:

FIG. 5a is a perspective view of a source gripping device in accordance with one embodiment of the invention;

FIG. 5b is an exploded view of the source gripping device of FIG. 5a in accordance with one embodiment of the invention;

FIG. 9a is a perspective view of a source holder device in accordance with one embodiment of the invention;

FIG. 9b is an exploded view of the source holder device of FIG. 9a in accordance with one embodiment of the invention;

DETAILED DESCRIPTION OF THE INVENTION

A source loading apparatus for an imaging system is disclosed in which a transmission source is advanced from a storage container, through the use of a translation device, into a holder device so that the transmission source can be rotated around the inside perimeter of the detector rings. The source loading apparatus provides a mechanism whereby the transmission source travels back and forth along one axis of motion, from a storage position to a loading position (i.e., from the storage position, rotation or adjustment vertically or side to side is not needed to advance transmission source into holder device). In the storage position, the transmission source, which is comprised of radioactive material, is safely shielded within the storage container. When needed for scanning, the transmission source is advanced from within the storage container into a holder device attached to the transmission ring. Once scanning is complete, the transmission source is removed from the holder device and returned to its storage position inside the storage container.

Figure 1:
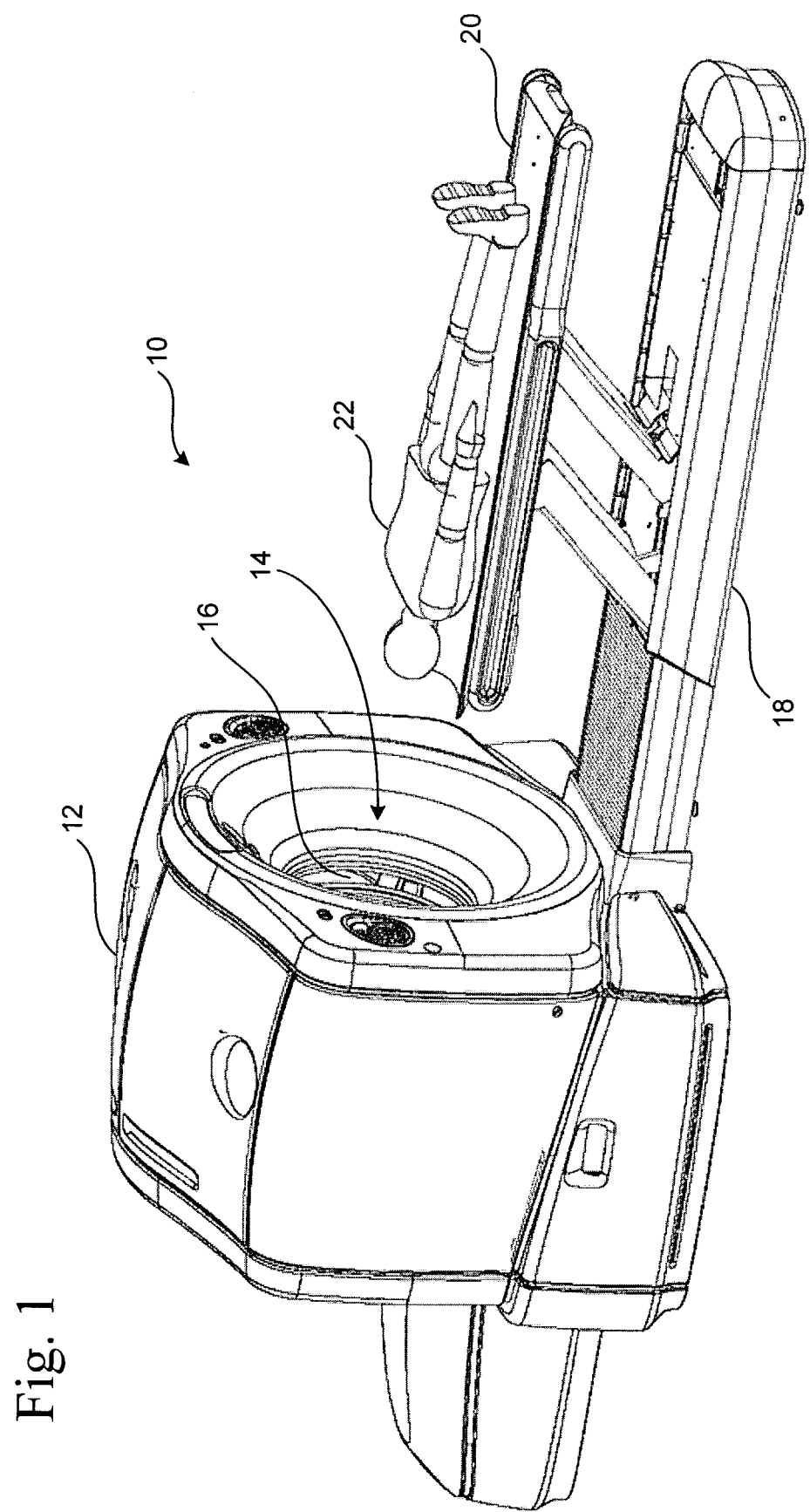
FIG. 1 is a perspective view of an illustrative imaging system in accordance with one embodiment of the invention.

FIG. 1 is a perspective view of an illustrative imaging system in accordance with one embodiment of the invention. Imaging system 10 is shown with gantry 12 and patient table 18. As shown in FIG. 1, gantry 12 includes patient bore 14, which is partially defined by detector ring 16. Table 18 is shown with patient 22 resting in the patient cradle 20. Patient cradle 20 is adapted to move into patient bore 14 such that the patient 22 can be scanned by the detector ring 16.

In this embodiment of the invention, imaging system 10 is a combined PET and Computed Tomography (CT) scanner. It should be appreciated that further embodiments of the imaging system may be PET or CT alone.

Figure 2:
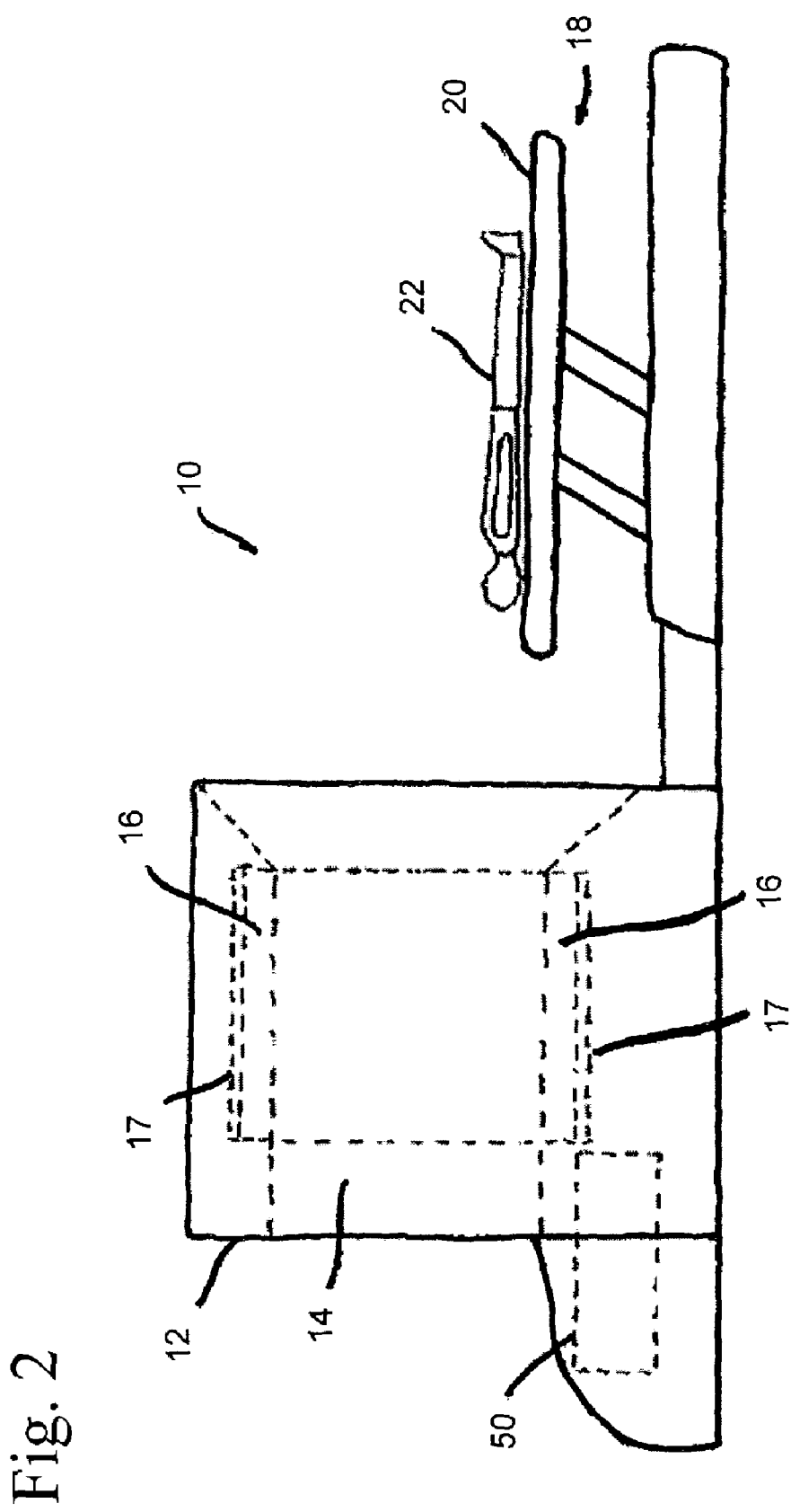
FIG. 2 is a side view of an imaging system in accordance with one embodiment of the invention.

FIG. 2 is a side view of the imaging system of FIG. 1. Within gantry 12, transmission ring 17 is adapted to rotate a transmission source around the detector ring 16 so that a series of detectors in detector ring 16 may be used to obtain an image of patient 22 being scanned. A source loading apparatus 50 is used to store the transmission source when not in use, and positioned adjacent to transmission ring 17. Source loading apparatus 50 is adapted for advancing the transmission source into a Source holder device attached to transmission ring 17 for use in scanning. The holder device is attached to transmission ring 17 such that when the transmission source is rotated around the patient bore 14, detector ring 16 gathers data on the coincidence events observed and transmits the data to a processing machine for producing the desired imaging.

Figure 3:
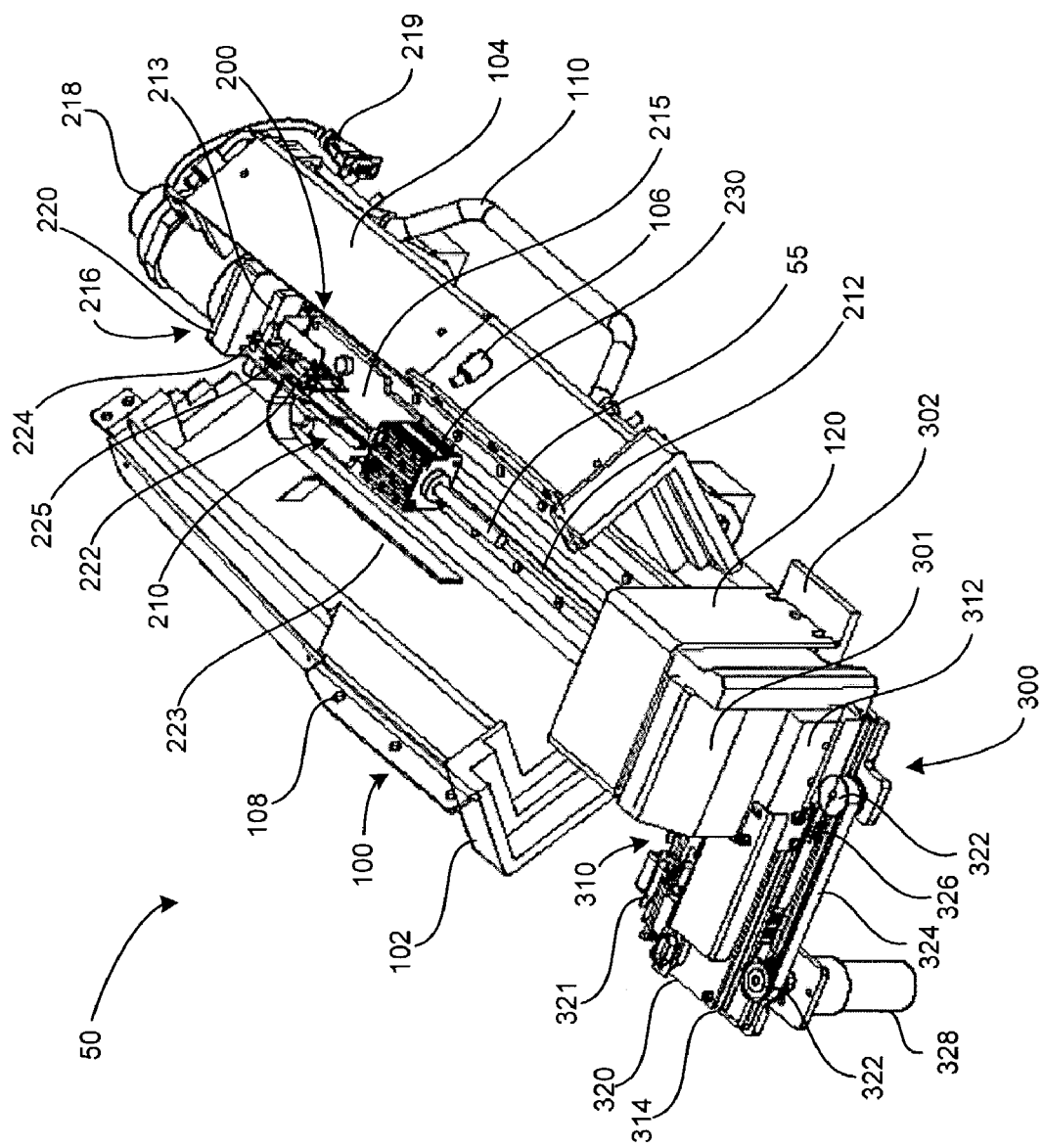
FIG. 3 is a perspective view of a source loading apparatus in accordance with one embodiment of the invention.
Figure 4:
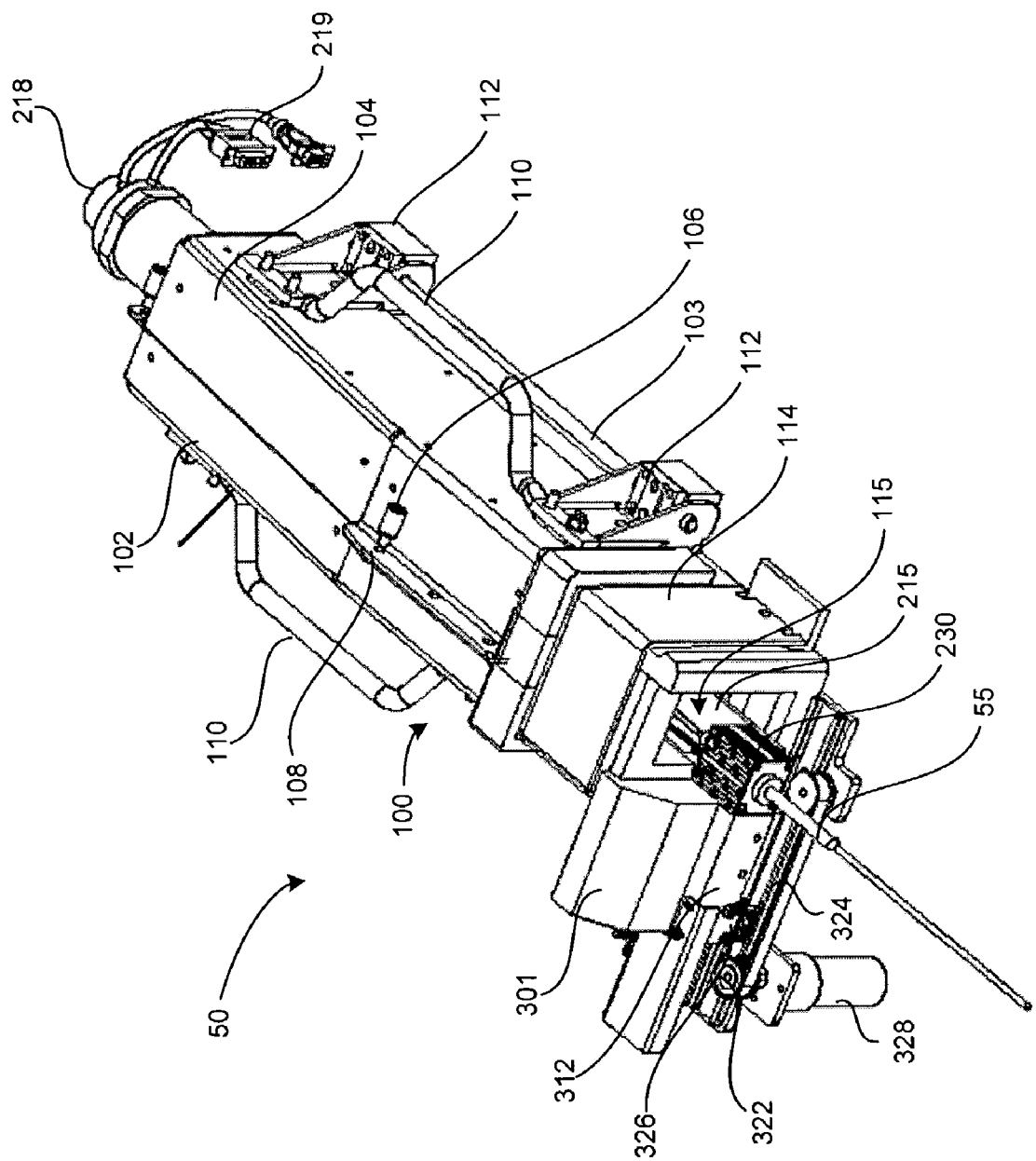
FIG. 4 is a perspective view of a source loading apparatus in accordance with one embodiment of the invention.

FIGS. 3 and 4 are perspective views of a source loading apparatus in accordance with one embodiment of the invention. As shown in FIG. 3, source loading apparatus 50 includes storage container 100, translation device 200, and door assembly 300. Storage container 100 provides the housing in which the transmission source 55 is kept when not being used.

In this embodiment, transmission source 55 is a source pin including a radioactive material, such as positron emitter Germanium 68. Transmission source 55 is cylindrically shaped and, configured for insertion into a holder device so that transmission source 55 can be rotated around the detector ring of the imaging system. Transmission source 55 may also include a radioactive portion and a non-radioactive portion, for insertion into a source gripping device. Storage container 100 is constructed of a radioactive shielding material, such as lead or tungsten, to prevent the penetration of radiation from storage container 100 when transmission source 55 is not in use.

Storage container 100 is comprised of right shield portion 102, left shield portion 104, bottom shield portion 103, and access port member 114. As shown in FIG. 3, storage container 100 is in the open position, i.e., the right shield 102 and left shield 104 are not engaged. Right shield 102 and left shield 104 are both hingedly attached to bottom portion 103 by pivot rod hinges 112, such that right shield 102 and left shield 104 are adapted to engage each other to form an elongate channel in which the translation device 200 is provided. As shown in FIG. 3, in this embodiment, right shield 102 and left shield are l-shaped members, rotatable around the pivot point of pivot rod hinge 112.

Right shield 102 and left shield 104 are secured together when pin 106, attached to the left shield 104 on the outside of storage container 100, engages pin slot 108, attached to the right shield 102. In this embodiment, a sheet metal piece is attached to the upper portion of both right shield 102 and left shield 104, each sheet metal piece including pin slots for receiving pin 106. To engage the right shield 102 and left shield 104, pin 106 is inserted through a pin slot in the metal piece attached to left shield 104, and further through a pin slot 108 on the metal piece attached to right shield 102, before it releasably secures both shield portion together. It should be appreciated that additional pin and pin slot arrangements may be utilized on the shield portions to provide for additional securing force between the two portions.

Pivot rod hinges 112 are attached to right shield 102 and left shield 104 to facilitate the opening of storage container 100 when pin 106 is disengaged from pin slot 108. Right shield 102 and left shield 104 also have shoulders, or recesses, formed within the front edge of each, such that when storage container 100 is closed, the shoulders of right shield 102 and left shield 104 engage, or enclose a portion of, access port member 120. Access port member 120 is a channel-type member, through which an access port 115 is formed such that transmission source 55 is advanced into the holder device of the transmission ring.

It should be appreciated that the mechanical parts that attach right shield 102, bottom 103, and left shield 104 to the pivot rod hinges 112, are used in a manner that does not affect the shielding properties of storage container 100. When right shield 102 and left shield 104 are engaged, the interior of storage container 100 is enclosed with the exception of access port 115 within access port member 120. However, as shown in FIG. 3, access door 301, of door assembly 300 covers access port 115 when transmission source 55 is in the storage position inside storage container 100.

Although not illustrated, it should be appreciated that further embodiment for the storage container may be utilized that allow for the storage of the transmission source when not is use. In one such embodiment, the storage container may comprise a container housing and a lid. The container housing may include a rear wall, side walls, and a front wall, which forms the base of a lid seat. The lid would be configured to fit within the lid seat, such that the lid provides the top of the storage container. The container housing would further include a bottom, from which each wall extends upwardly. The front wall would have an opening formed within it, i.e., an access port, through which the transmission source would be advanced into the holder device of the transmission ring. When the lid is placed on the lid seat, the interior of the storage container would be enclosed with the exception of the access port. An access door, of the door assembly would cover the access port when the transmission source is in storage position inside storage container.

Translation device 200 also includes source gripping device 230, which is responsible for securing transmission source 55 by retaining a portion of transmission source 55 using magnetic forces. When enclosed and shielded by storage container 100 and access door 301, transmission source 55 is considered to be in a storage position. Illustratively, FIG. 3 depicts source loading apparatus 50 and transmission source 55 in a storage position, with the exception that right shield 102 and left shield 104 are not engaged.

To allow the transmission source to be stored within and advanced out from within storage container 100, portions of translation device 200 are located within storage container 100. Translation device 200 includes drive assembly 210 and source gripping device 230. Drive assembly 210 advances source gripping device 230 back and forth between the storage position and loading position. Source gripping device 230 holds transmission source 55 in the storage position and transfers transmission source 55 to the holder device for scanning.

As described above, FIG. 3 depicts a storage position of transmission source 55. In this position, access door 301 covers access port 115 to enclose the interior of storage container 100. Similar to storage container 100, access door 301 is also constructed of a radioactive shielding material, such as lead or tungsten. When signaled, door drive assembly 310 moves access door 301 from its storage position covering access port 115 to its loading position wherein access port 115 is exposed such that transmission source 55 can be advanced through access port 115, as shown in FIG. 4.

In this embodiment, door assembly 300 is comprised of access door 301 and door drive assembly 310. As shown in FIG. 3, door drive assembly 310 utilizes a pulley/timing belt system to move access door 301 and expose access port 115. The pulley/timing belt system includes control device 320, connectors 321, groove pulleys 322, timing belt 324, belt fastener 326 and motor 328. Timing belt 324 is driven by groove pulleys 322, which are powered by motor 328 under the command of control device 320. Belt fastener 326, or belt crimp, attaches to timing belt 324, and is also affixed to door mount 312. A portion of the lower half of access door 301 is secured to door mount 312. Accordingly, when timing belt 324 is driven by motor 328 using groove pulleys 322, belt fastener 326 pulls door mount 312 along, which in turn moves access door 301 aside, exposing access port 115.

Control device 320 is in communication with control portion 216, such that when source gripping device 230 is advanced forward, control device 320 receives a signal to move access door 301. In this embodiment of the invention, control device 320 is a Printed Circuit Board ("PCB"). It should be appreciated that control portion 216 may send a signal indicating movement of the transmission source to a processing machine, which in turn will send a command to control device 320 through connectors 321 to move access door 301.

As shown in FIG. 4, transmission source 55 and source gripping device 230 are no longer in the storage position depicted in FIG. 3. Right shield 102 and left shield 104 are engaged, enclosing the interior of storage container 100. Transmission source 55 and source gripping device 230 are in a loading position, wherein source gripping device 230 is at a loading point and adapted for alignment with the holder device of the transmission ring. In the loading position, both source gripping device 230 and the holder device would each retain a portion of the transmission source 55, which would have been inserted into the holder device by the forward advancement of source gripping device 230. As shown in FIG. 4, access door 300 has been moved aside exposing access port 115 and allowing source gripping device 230 to advance through the opening. It should be appreciated that the loading position depicted in FIG. 4 may also represent the positioning of source gripping device 230 at the unloading position, in which source gripping device 230 grabs transmission source 55 from the holder device and retracts inside storage container 100.

As shown in FIG. 4, right shield 102 and left shield 104 have handles 110 attached to their side portions. Handles 110 facilitate the opening of storage container 100 when right shield 102 and left shield 104 are separated. Handles 110 may also be utilized as stands when right shield 102 and left shield 104 separate and rotate away from the other using pivot rod hinges 112. With pivot rod hinges 112, right shield 102 and left shield 104 are attached to the bottom portion (not illustrated) of storage container 100.

FIG. 5a is a perspective view of a source gripping device in accordance with one embodiment of the invention. FIG. 5b illustrates an exploded view of the source gripping device of FIG. 5a. In this embodiment, source gripping device 230 is comprised of housing 232, electromagnet portion 234, magnet ring 240 and magnet cover 242. Electromagnet portion 234 and magnet ring 240 provide the magnetic holding forces utilized by the source gripping device 230 in the storage, loading and unloading of transmission sources.

As shown in FIG. 5b, electromagnet portion 234 is comprised of electromagnet housing 236 and electromagnet core 238. When assembled, electromagnet housing 236 substantially encloses electromagnet core 238, and is secured within cavity 233 of housing 232. In this embodiment, electromagnet core 238 is a tubular member with a disc-shaped head and an inner diameter configured for receiving at least a portion of the transmission source. The tubular member of electromagnet core 238 is constructed of a series of copper windings forming a coil around a steel sleeve. Electromagnet core 238 is designed to slide within cavity 237 of electromagnet housing 236. Connector 235 is attached to electromagnet housing 236 and provides the electricity to the electromagnet 234 so that it can be energized.

Magnet ring 240 is aligned adjacent to the disc-shaped head of electromagnet core 238, and magnet cover 242 is affixed to housing 232, enclosing the electromagnetic portion 234 and magnet ring 240. In this embodiment, magnet cover 242 is constructed of stainless steel sheet metal, and suitable fasteners, such as screws or bolts, may be inserted into holes 244 to affix magnet cover 242 to housing 232.

Source gripping device 230, utilizes inner cavity 231 for receiving at least a portion of the transmission source. Inner cavity 231 of source gripping device 230 is defined by bore sleeve 239 of electromagnet core 238, and openings 241 and 243, extending through magnet ring 240 and magnet cover 242, respectively. In this embodiment, source gripping device 230 is formed such that a transmission source can be inserted into cavity 231, which comprises the retaining portion of source gripping device 230. Sensor 246 is affixed to the rear of housing 232 and is adapted for detecting the presence of the transmission source within inner cavity 231. Sensor 246 may be axially aligned on the rear of housing 232 and may comprise a normally open—Positive-Negative-Positive (PNP) inductive sensor.

Figure 6:
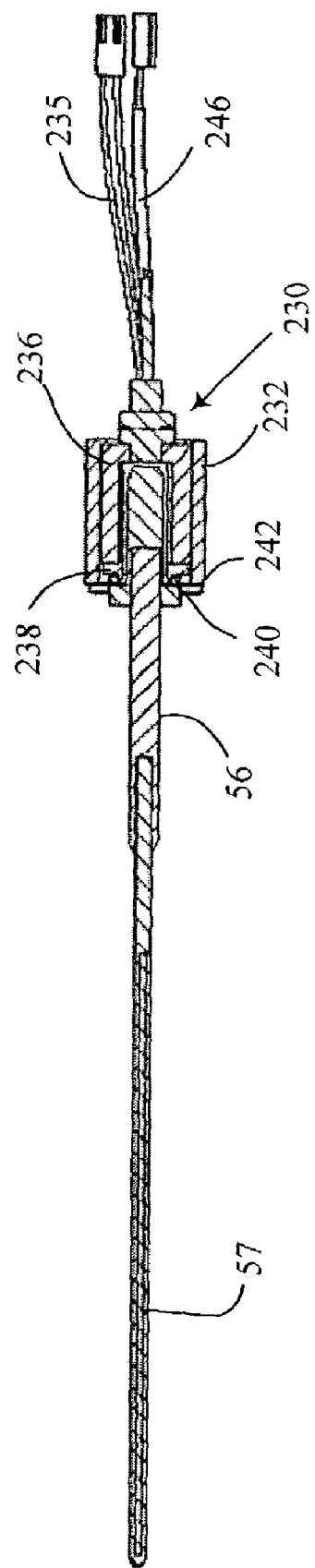
FIG. 6 is a planar sectional view of a source gripping device with transmission source in accordance with one embodiment of the invention.

As described above, magnet ring 240 and electromagnet portion 234 provide the magnetic holding forces used in the securing, loading and unloading of transmission sources in accordance with an exemplary embodiment of the invention. FIG. 6 is a planar sectional view of source gripping device of holding a transmission source in accordance with one embodiment of the invention. As shown in FIG. 6, transmission source 55 includes a non-radioactive portion 56, which source gripping device 230 is retaining at least a part of, and a radioactive portion 57, which is designed to release the radiation used in the imaging system. Magnet ring 240 is a permanent magnet and provides a first magnetic holding force for securing the transmission source 55. In this embodiment, magnet ring 240 is constructed of Neodymium 37, and possesses a magnetic holding force equal to 1.2 lbf. However, it should be appreciated that magnet ring 240 may be constructed of any suitable magnetized material having an associated holding force.

Electromagnet portion 234 is designed to produce a magnetic holding force upon activation, i.e., when an electric current is passed through the windings of electromagnet core 238. Together, the magnetic holding forces of magnet ring 240 and electromagnet portion 234 produce a combined magnetic holding force greater than the magnetic holding force of the transmission ring's holder device, described in further detail below.

It should be appreciated that source gripping device 230 is designed such that when transmission source 55 is in its storage position (as depicted in FIG. 3), the only magnetic holding force needed to secure transmission source 55 in the inner cavity 231 of source gripping device 230 is that produced by magnet ring 240.

To load the transmission source, source gripping device 230 is advanced to a loading position where it is aligned with the holder device. During this alignment, the radioactive portion 57 of transmission source 55 is inserted into the holder device. The holder device utilizes a permanent magnet ring, or a series of magnet rings, to produce a magnetic holding force greater than the holding force of magnet ring 240 alone. Consequently, during the loading process, when both source gripping device 230 and the holder device are holding a portion of the transmission source, the stronger magnetic holding force of the holder device retains transmission source 55 when source gripping device 230 is retracted into storage container 100. It should be appreciated that the holder device may utilize any combination of magnets to retain the transmission source from source gripping device 230, as long as the combination produces a holding force greater than that of magnet ring 240, but less than the combined holding force of magnet ring 240 and electromagnet portion 234.

After loading of the transmission source into the holder device, source gripping device 230 is driven back away from the holder device, leaving the transmission source in the holder device so that it may be utilized in the imaging system. Once the scanning is complete and transmission source 55 is no longer needed, source gripping device 230 is once again aligned with the holder device so that each is holding a portion of transmission source 55. Electromagnet portion 234 is then energized producing a magnetic holding force that either alone, or in combination with the holding force of magnet ring 240, overpowers the Source holder device's magnetic holding force. Thus, electromagnet portion 234 allows source gripping device 230 to pull transmission source 55 from the holder device and return the transmission source 55 to its storage position within the storage container. Therefore, source gripping device 230 is adapted for utilizing at least two different magnetic holding forces, including: (1) produced by magnet ring 240, such that it is overpowered by the holder device upon source loading, and (2) the combined force produced upon energizing of electromagnet portion 234, which is stronger than the holder device holding force for unloading.

Figure 7:
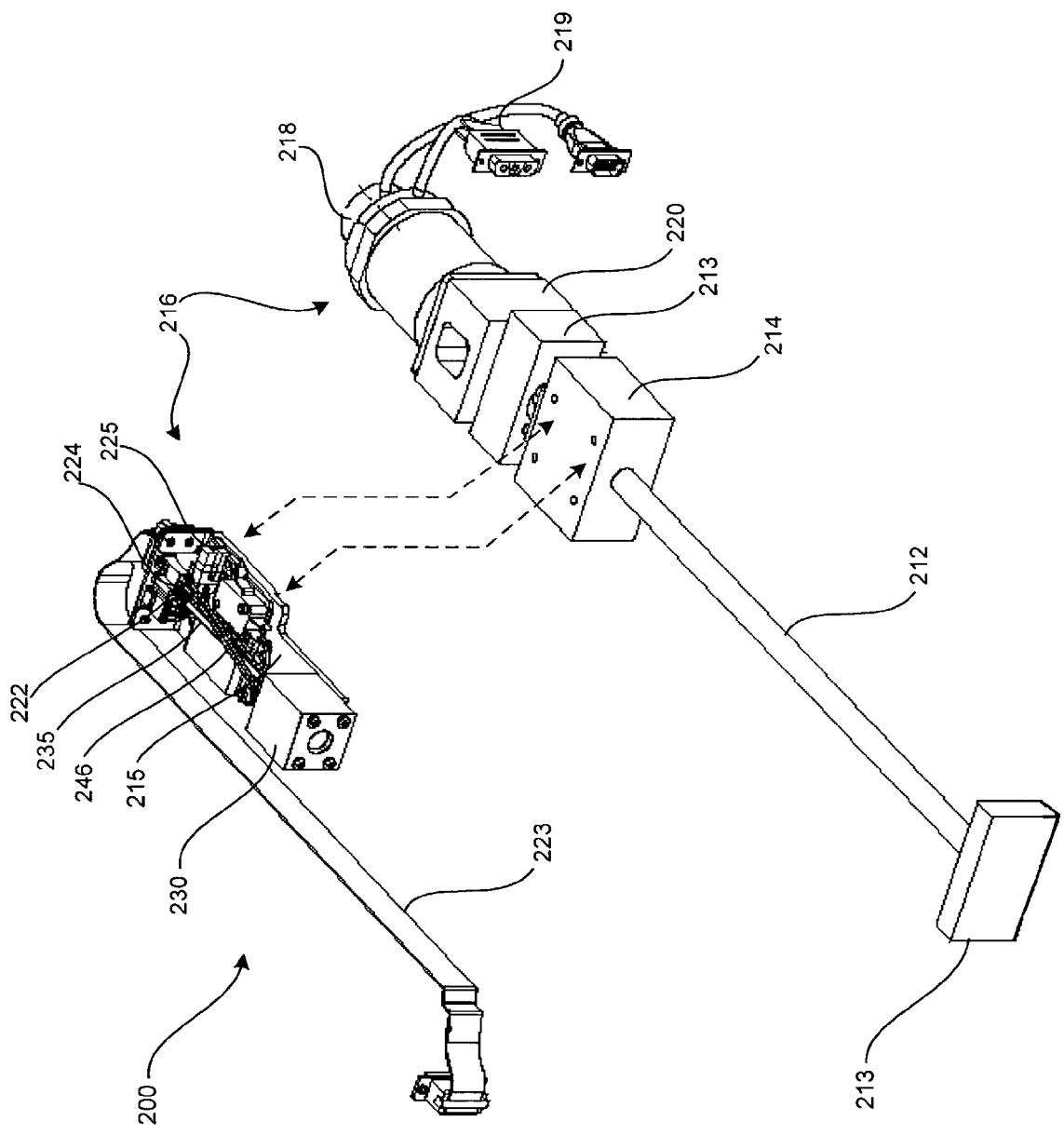
FIG. 7 is an exploded perspective view of translation device in accordance with one embodiment of the invention.

FIG. 7 is a perspective view of the translation device of FIGS. 3 and 4 in accordance with one embodiment of the invention. As shown in FIG. 7, translation device 200 is illustrated in an exploded view. Translation device 200 comprises drive assembly 210 and source gripping device 230. In this embodiment of the invention, drive assembly 210 includes lead screw 212, bearing blocks 213, carriage 214, adapter plate 215 and control portion 216. Source gripping device 230 is mounted on adapter plate 215, which is designed for attachment to carriage 214. Carriage 214 is slidably attached to lead screw 212. Lead screw 212 extends between bearing blocks 213, which are adapted for positioning inside the storage container at the base of the rear and front walls. Control portion 216 controls the movement of carriage 214 along the lead screw 212, such that when the transmission source is needed for scanning, control portion 216 drives carriage 214 forward to a loading point where the source gripping device loads the transmission source into the holder device.

Control portion 216 utilizes motor 218 to drive carriage 214 along the lead screw 212. Motor 218 is electronically coupled to and powers carriage 214 along lead screw 212. Motor 218 is attached to motor mount 220. In this embodiment, motor 218 is a brushless DC servo motor adapted for electronic coupling to and communication with a processing machine controlling the operation of an imaging system. Accordingly, motor 218 may receive input from and generate output to a processing machine through connectors 219, or ribbon cable 223, which is in communication with circuit board 222.

In the storage position, the access door covers the access port. When the transmission source must be loaded, the access door is moved aside by the door drive assembly. Accordingly, control portion 216 utilizes sensor 224 to alert the door drive assembly when carriage 214 and source gripping device 230 begin advancing towards the access port. Sensor 224 signals the door drive assembly to move the access door aside to expose the access port through which the transmission source will travel. In this embodiment, sensor 224 may comprise an optical sensor, or switch, that detects when carriage 214 or source gripping device 230 are moved from the storage position towards the loading position through coordination with actuator 225. It should be appreciated that sensor 224 may signal the movement of carriage 214 or source gripping device 230 by sending an electronic signal to a processing machine, which in turn will command the door drive assembly to move access door.

Figure 8:
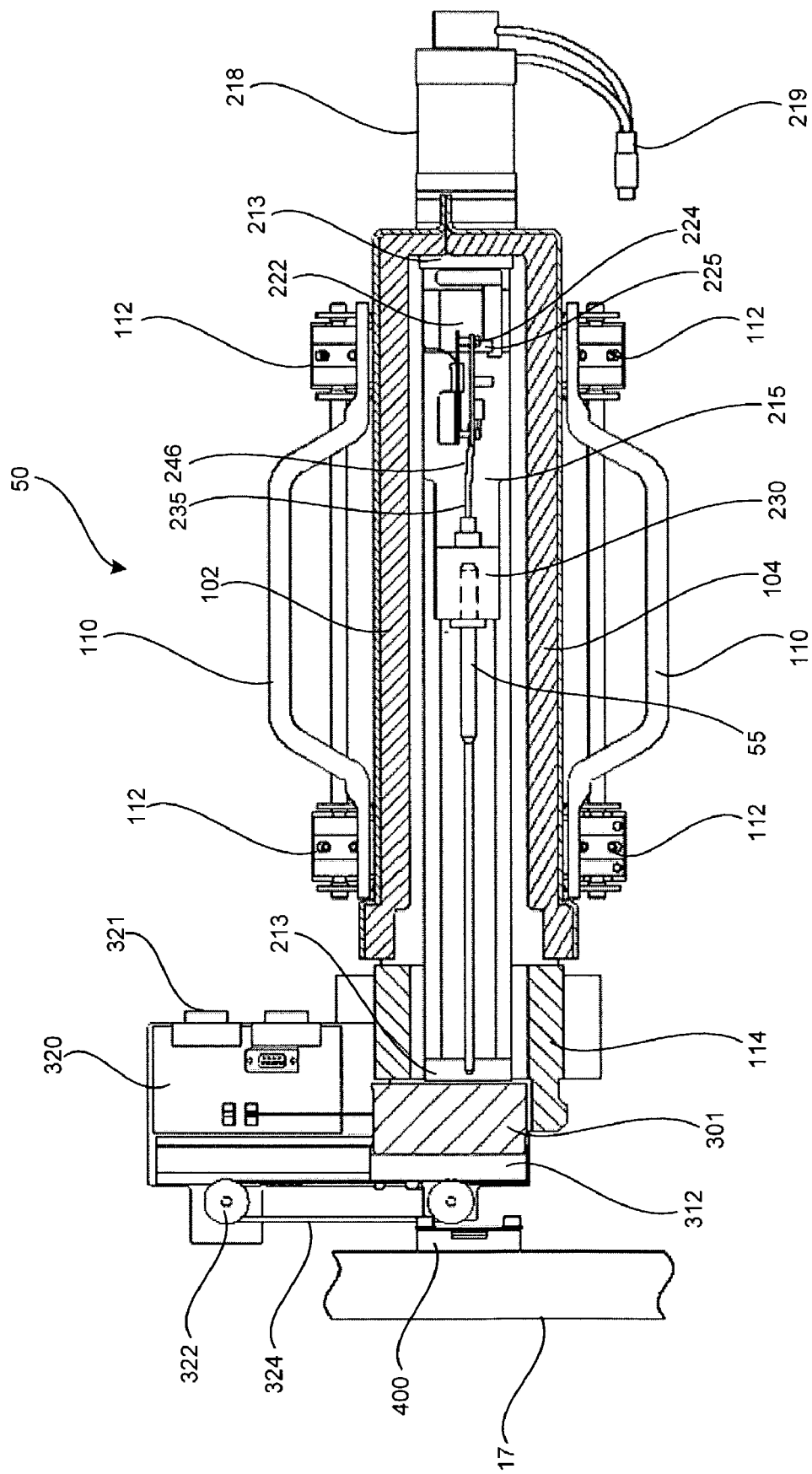
FIG. 8 is a planar view of a source loading apparatus in accordance with one embodiment of the invention.

FIG. 8 is a planar sectional view of a source loading apparatus with transmission source and transmission ring in accordance with one embodiment of the invention. As shown in FIG. 8, source loading apparatus 50 is in the storage position, i.e., transmission source 55 is held by source gripping device 230 and both are enclosed within storage container 100. Source loading apparatus 50 is also aligned with holder device 400, which is attached to transmission ring 17, and positioned to deliver transmission source 55 into holder device 400 attached to transmission ring 17. Holder device 400 is attached to transmission ring 17 such that when transmission source 55 is delivered into holder device 400, transmission ring 17 rotates the holder device 400 around the patient bore, and the detector ring gathers the imaging data.

FIG. 9a is a perspective view of the source holder device of FIG. 8 in further detail in accordance with one embodiment of the invention, as shown in an exploded view in FIG. 9b. Holder device 400 includes housing 402, magnet rings 410 and 412, and cover 414. Housing 402 includes a recess 404 from which cylinder member 406 extends. Cylinder member 406 has bore 407 that extends axially through housing 402. Recess 404 and cylinder member 406 are configured such that magnet rings 410 and 412 can be fitted over the outer perimeter of cylinder member 406 within recess 404. Once the magnet rings 410 and 412 are secured on cylinder member 406, cover 414 is affixed to housing 402, enclosing the magnet rings and providing an axial bore through holder device 400 for receiving the transmission source from the source gripping device.

As described above, magnet rings 410 and 412 each possess a magnetic holding force. The combined magnetic holding force of magnet rings 410 and 412 is greater that that possessed by the magnet ring located within source gripping device 230, thus facilitating loading of the transmission source in the holder device 400. However, the combined magnetic holding force of magnet rings 410 and 412 is not greater than that of the magnet ring located within source gripping device 230 combined with the electromagnet holding force produced when the electromagnet portion 234 within source gripping device 230 is energized. It should be appreciated that although holder device 400 has been shown with two magnet rings, any suitable number of magnet rings or strength of magnet(s) may be utilized so that the magnetic holding force of the holder device 400 is greater than the magnetic holding force produced by the magnet ring 240 in the source gripping device 230, but less than the combined magnetic holding force of the magnet ring 240 and electromagnet portion 234 in the source gripping device 230.

Figure 10:
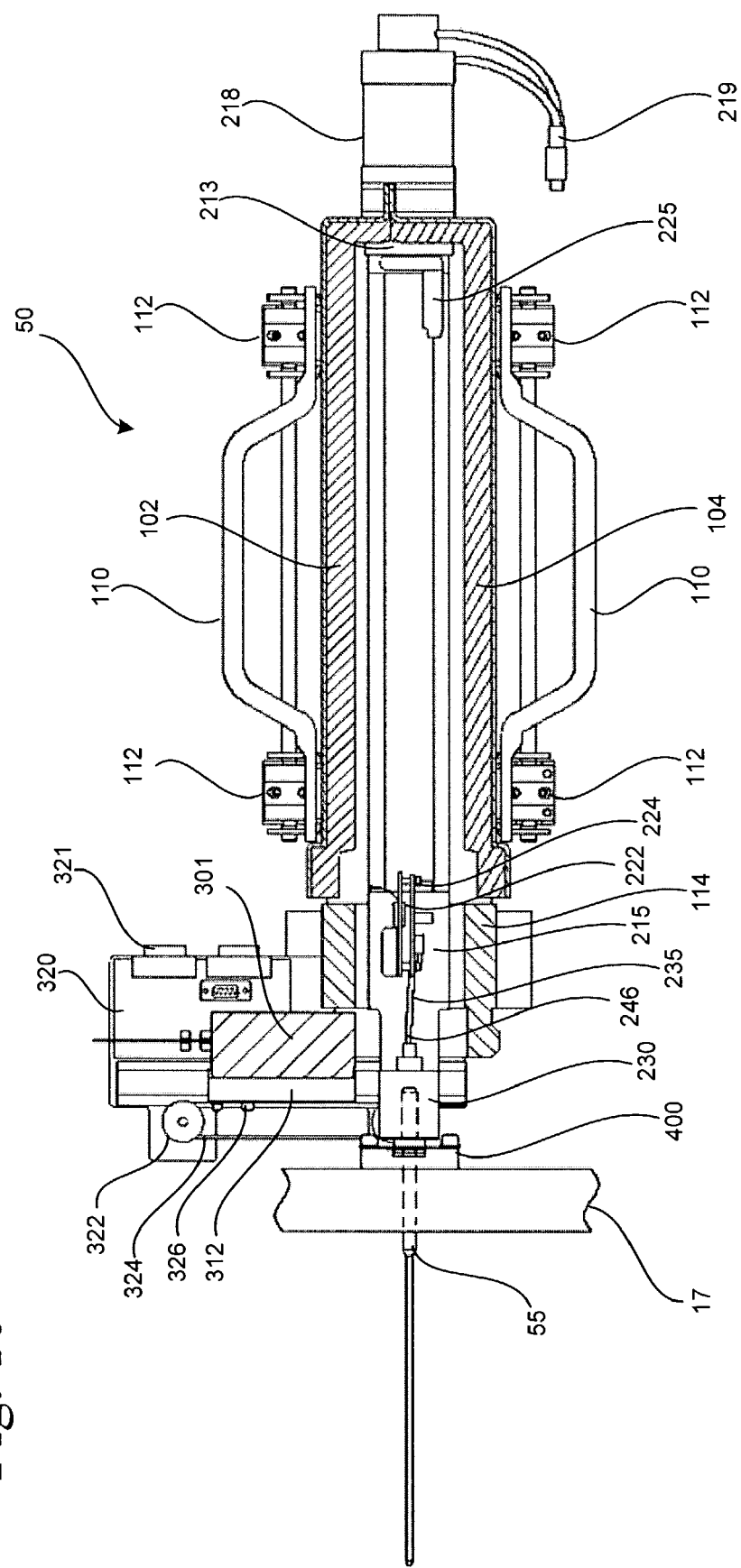
FIG. 10 is a planar view of a source loading apparatus in accordance with one embodiment of the invention.
Figure 11:
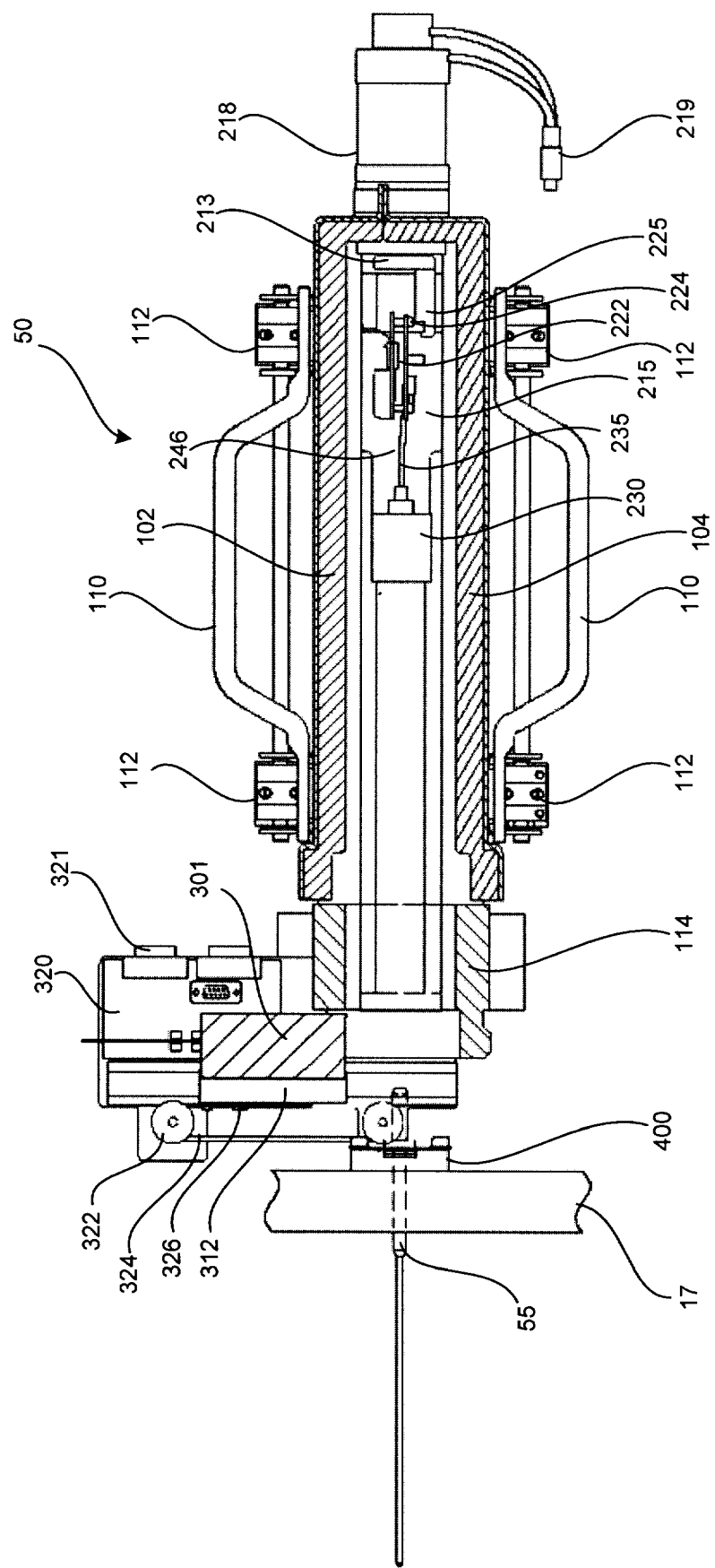
FIG. 11 is a planar view of a source loading apparatus in accordance with one embodiment of the invention.

FIGS. 10 and 11 are planar sectional views of source loading apparatuses in accordance with one embodiment of the invention. In FIG. 10, source gripping device 230 has been advanced forward to align with holder device 400, such that both source gripping device 230 and holder device 400 are each retaining a portion of transmission source 55. Once loading is complete, source gripping device 230 retracts into storage container 100, as shown in FIG. 11. However, as described above, transmission source 55 remains held in holder device 400 because of the greater combined magnetic holding force of the magnet rings 410 and 412.

When transmission source 55 is to be returned to the storage position, as source gripping device 230 and holder device 400 realign in the loading position shown in FIG. 10. The electromagnet portion 234 of source gripping device 230 is energized, which produces a combined magnetic holding greater than that of magnet rings 410 and 412. Thus, source gripping device 230 removes transmission source 55 from holder device 400 and retracts into storage container 100, as shown in FIG. 8.

FIGS. 1–11 illustrate an embodiment of the invention in which a source loading apparatus utilizes a translation device to advance a transmission source from a storage position inside a shielded storage container to a loading position aligned with the holder device of a transmission ring. In further embodiments of the invention, the translation device may employ a different drive assembly to advance the source gripping device carrying the transmission source. For example, the source gripping device may be mounted on a rack and pinion assembly, which would move the source gripping device back and forth from the storage and loading positions. Likewise, in other embodiments, the door assembly may utilize mechanisms other than the pulley timing belt system to move the access door to expose the access port. For example, the door drive assembly may include a rack and pinion gear assembly that moves the access door when the source gripping device is advanced forward. Additionally, a worm/worm gear assembly can be utilized with a lead screw that advances a carriage forward with the source gripping device and drives the access door aside.

As described above with reference to various embodiments of the invention, the source loading apparatus, or various components thereof, may receive input from or send output to a processing machine to accomplish the desired function of the invention. It should be appreciated that an imaging system, gantry, source loading apparatus, or components thereof, may receive commands from a controller workstation through the processing machine, or other mechanical components electronically coupled to or in communication with a processing machine. As used herein, the term "processing machine" is to be understood to include at least one processor that uses at least one memory. The memory stores a set of instructions. The instructions may be either permanently or temporarily stored in the memory or memories of the processing machine. The processor executes the instructions that are stored in the memory or memories in order to process data. The set of instructions may include various instructions that perform a particular task or tasks, such as those tasks described. Such a set of instructions for performing a particular task may be characterized as a program, software program, or simply software. As noted above, the processing machine executes the instructions that are stored in the memory or memories to process data. This processing of data may be in response to commands by a user or users of the processing machine, in response to previous processing, in response to a request by another processing machine and/or any other input, for example.

The processing machine used to implement the invention may be a general purpose computer. However, the processing machine described above may also utilize any of a wide variety of other technologies including a special purpose computer, a computer system including a microcomputer, mini-computer or mainframe, a programmed microprocessor, a micro-controller, an integrated circuit, a logic circuit, a digital signal processor, a programmable logic device, or any other device or arrangement of devices that is capable of implementing the invention.

Many embodiments and adaptations of the present invention other than those herein described, as well as many variations, modifications and equivalent arrangements, will be apparent from or reasonably suggested to those skilled in the art by the present invention and foregoing description thereof, without departing from the substance or scope of the invention.

While the present invention has been described here in detail in relation to its exemplary embodiments, it is to be understood that this disclosure is only illustrative and exemplary of the present invention and is made to provide an enabling disclosure of the invention. Accordingly, the foregoing disclosure is not intended to be construed or to limit the present invention or otherwise to exclude any other such embodiments, adaptations, variations, modifications or equivalent arrangements.

The invention claimed is:

1. A transmission source loading apparatus for an imaging system utilizing a transmission source, comprising:
   a storage container for storing the transmission source; and
   a translation device, the translation device being adapted for advancing the transmission source from the storage container into a holder device for use of the imaging system, wherein the advancement of the transmission source is caused by a linear movement of the translation device without any rotational movement thereof.

2. The apparatus of claim 1, wherein an access door is located proximate to the storage container, the translation device being adapted for advancing at least a first portion of the transmission source into the holder device through an access port exposed by displacing the access door.

3. The apparatus of claim 2, wherein the translation device further includes:
   a drive assembly; and
   a source gripping device for retaining at least a second portion of the transmission source, the drive assembly being adapted for advancing the source gripping device to a loading point proximate to the access port.

4. The apparatus of claim 3, wherein the source gripping device includes:
   a housing;
   a first magnet portion fixed to the housing, the first magnet portion having a first magnetic holding force; and
   an electromagnet portion fixed to the housing, the electromagnet portion producing a second magnetic holding force when activated.

5. The apparatus of claim 4, wherein the holder device includes:
   a housing;
   a source receiving portion disposed in the housing; and
   a third magnet portion fixed to the housing, the third magnetic portion having a third magnetic holding force.

6. The apparatus of claim 5, wherein the third magnetic holding force is greater than the first magnetic holding force.

7. The apparatus of claim 6, wherein the holder device and source gripping device are adapted for alignment at the loading point such that when the at least first portion of the transmission source is advanced into the source receiving portion of the holder device, the third magnetic holding force being greater than the first magnetic holding force, the transmission source is retained by the source receiving portion of the holder device.

8. The apparatus of claim 5, wherein the first magnetic holding force and the second magnetic holding force combined are greater than the third magnetic holding force.

9. The apparatus of claim 8, wherein the holder device and source gripping device are adapted for alignment at the loading point such that when the transmission source is advanced into the source receiving portion of the holder device, the first magnetic holding force and the second magnetic holding force combined being greater than the third magnetic holding force, the transmission source is retained by the source gripping device.

10. The apparatus of claim 3, wherein the drive assembly includes:
    a carriage mounted on a lead screw, the carriage controllably translated along the lead screw by a control portion.

11. The apparatus of claim 10, wherein the control portion includes a servo motor.

12. The apparatus of claim 10, wherein the source gripping device is mounted on the carriage.

13. The apparatus of claim 3, wherein the source gripping device and at least a portion of the drive assembly are housed within the storage container.

14. The apparatus of claim 2, wherein the access door is coupled to a door drive assembly, the door drive assembly being adapted for displacing the access door to expose the access port.

15. The apparatus of claim 14, wherein the door drive assembly includes:
    a door mount fixed to the access door;
    a track assembly; and
    a control device being adapted for controllably displacing the door mounted along the track assembly.

16. The apparatus of claim 15, wherein the control device includes a pulley timing belt system coupled to the door mount for controllably displacing the access door.

17. The apparatus of claim 1, wherein the translation device is adapted for advancing the transmission source from the storage container into the holder device along a single axis of motion.

18. The apparatus of claim 1, wherein at least a portion of the translation device is housed within the storage container when the transmission source is in storage.

19. The apparatus of claim 1, wherein the translation device is engaged with the transmission source when the transmission source is in storage.

20. A transmission source loading apparatus for an imaging system utilizing a transmission source, comprising:
    means for storing the transmission source; and
    means for advancing the transmission source from the storage means into a means for rotating the transmission source for use of the imaging system, wherein the advancement of the transmission source is caused by a linear movement of the advancing means without any rotational movement thereof.

21. The apparatus of claim 20, wherein an access door is located proximate to the storage means, the means for advancing the transmission source being adapted for advancing at least a first portion of the transmission source into the means for rotating through an access port exposed by displacing the access door.

22. The apparatus of claim 20, wherein the means for advancing the transmission source is adapted for advancing the transmission source from the storage means into the holder means along a single axis of motion.

23. The apparatus of claim 20, wherein at least a portion of the advancing means is housed within the storage means when the transmission source is in storage.

24. The apparatus of claim 20, wherein the advancing means is engaged with the transmission source when the transmission source is in storage.

* * * * *

UNITED STATES PATENT AND TRADEMARK OFFICE
CERTIFICATE OF CORRECTION

PATENT NO. : 7,126,142 B2
APPLICATION NO. : 10/285014
DATED : October 24, 2006
INVENTOR(S) : Thomas R. Murray et al.

It is certified that error appears in the above-identified patent and that said Letters Patent is hereby corrected as shown below:

On the Title Page Item (75) in "Inventors" field, replace inventor name "Timithoy F. Hamers" with --Timothy F. Hamers--

Signed and Sealed this

Tenth Day of July, 2007

JON W. DUDAS
*Director of the United States Patent and Trademark Office*